United States Patent
Goodwill

(10) Patent No.: US 10,775,452 B2
(45) Date of Patent: Sep. 15, 2020

(54) MAGNETIC PARTICLE IMAGING

(71) Applicants: Magnetic Insight, Inc., Alameda, CA (US); University of California at Berkeley, Berkeley, CA (US)

(72) Inventor: Patrick W. Goodwill, Oakland, CA (US)

(73) Assignees: MAGNETIC INSIGHT, INC., Alameda, CA (US); UNIVERSITY OF CALIFORNIA AT BERKELEY, Berkely, CA (US)

( * ) Notice: Subject to any disclaimer, the term of this patent is extended or adjusted under 35 U.S.C. 154(b) by 296 days.

(21) Appl. No.: 15/648,403

(22) Filed: Jul. 12, 2017

(65) Prior Publication Data
US 2018/0017640 A1 Jan. 18, 2018

Related U.S. Application Data

(60) Provisional application No. 62/361,463, filed on Jul. 12, 2016, provisional application No. 62/361,475, filed on Jul. 12, 2016.

(51) Int. Cl.
| | | |
|---|---|---|
| G01R 33/12 | (2006.01) | |
| G01R 33/02 | (2006.01) | |
| G01N 27/72 | (2006.01) | |
| G01R 33/10 | (2006.01) | |
| A61B 5/05 | (2006.01) | |

(52) U.S. Cl.
CPC ........ *G01R 33/1276* (2013.01); *A61B 5/0515* (2013.01); *G01N 27/72* (2013.01); *G01R 33/0213* (2013.01); *G01R 33/10* (2013.01)

(58) Field of Classification Search
CPC .. A61B 5/0515; G01N 27/72; G01R 33/0213; G01R 33/10; G01R 33/1276
See application file for complete search history.

(56) References Cited

U.S. PATENT DOCUMENTS

| | | | |
|---|---|---|---|
| 4,538,130 | A | 8/1985 | Gluckstern |
| 4,545,384 | A | 10/1985 | Kawachi |
| 5,004,983 | A | 4/1991 | Proksa |
| 5,510,711 | A | 4/1996 | Molyneaux |

(Continued)

FOREIGN PATENT DOCUMENTS

| | | |
|---|---|---|
| EP | 2547253 | 1/2013 |
| EP | 3143929 | 3/2017 |

(Continued)

OTHER PUBLICATIONS

Biederer, S et al.; "A Spectrometer for Magnetic Particle Imaging," IFMBE Proceedings (International Federation for Medical and Biological Engineering), Springer, DE, vol. 22, No. 3, Feb. 4, 2009, pp. 2313-2316, XP009130408, ISSN: 1680-0737, DOI: 10.1007/978-3-540-89208-3_555.

(Continued)

*Primary Examiner* — Rishi R Patel
(74) *Attorney, Agent, or Firm* — Pillsbury Winthrop Shaw Pittman LLP

(57) ABSTRACT

A Magnetic Particle Imaging (MPI) system with a magnet configured to generate a magnetic field having a field free line, the system including at least one shim magnet configured to modify the magnetic field in a manner to maintain desired magnetic flux distributions during imaging.

17 Claims, 15 Drawing Sheets

(56) References Cited

U.S. PATENT DOCUMENTS

| | | | |
|---|---|---|---|
| 5,965,214 | A | 10/1999 | Crossfield |
| 6,054,924 | A | 4/2000 | Dames |
| 6,076,007 | A | 6/2000 | England |
| 6,144,300 | A | 11/2000 | Dames |
| 6,204,766 | B1 | 3/2001 | Crossfield |
| 6,230,972 | B1 | 5/2001 | Dames |
| 6,323,769 | B1 | 11/2001 | Dames |
| 6,369,965 | B1 | 4/2002 | Dames |
| 6,486,655 | B1 | 11/2002 | Crossfield |
| 6,577,237 | B1 | 6/2003 | Dames |
| 6,595,419 | B1 | 7/2003 | Doyle |
| 7,300,452 | B2 | 11/2007 | Gleich |
| 7,351,194 | B2 | 4/2008 | Gleich |
| 7,758,622 | B2 | 7/2010 | Gleich |
| 7,778,681 | B2 | 8/2010 | Gleich |
| 8,757,166 | B2 | 6/2014 | McKenna |
| 8,847,592 | B2 | 9/2014 | Goodwill |
| 8,884,617 | B2 | 11/2014 | Goodwill |
| 8,968,171 | B2 | 3/2015 | McKenna |
| 9,274,084 | B2 | 3/2016 | Goodwill |
| 9,364,165 | B2 | 6/2016 | Gleich |
| 9,417,302 | B2 | 8/2016 | Kuhn |
| 9,451,900 | B2 | 9/2016 | Boeve |
| 9,682,247 | B2 | 6/2017 | Susedik |
| 9,687,668 | B2 | 6/2017 | McKenna |
| 1,567,423 | A1 | 8/2017 | Goodwill |
| 9,763,594 | B2 | 9/2017 | Goodwill |
| 10,124,186 | B2 | 11/2018 | McKenna |
| 2003/0085703 | A1 | 5/2003 | Gleich |
| 2005/0073309 | A1 | 4/2005 | Williams |
| 2006/0211938 | A1 | 9/2006 | Gleich |
| 2006/0248944 | A1 | 11/2006 | Gleich |
| 2007/0258908 | A1 | 11/2007 | Lanza |
| 2008/0218162 | A1 | 9/2008 | Ruhrig |
| 2008/0309330 | A1 | 12/2008 | Ohyu |
| 2009/0115415 | A1 | 5/2009 | Weaver |
| 2010/0033171 | A1 | 2/2010 | Gleich |
| 2010/0052668 | A1 | 3/2010 | Gleich |
| 2011/0098558 | A1* | 4/2011 | Weaver ............... A61B 5/05 600/420 |
| 2011/0306870 | A1* | 12/2011 | Kuhn ............... A61B 5/0515 600/411 |
| 2012/0065491 | A1 | 3/2012 | Borgert |
| 2012/0100079 | A1 | 4/2012 | Burdinski |
| 2013/0241548 | A1* | 9/2013 | Gleich ............... G01R 33/44 324/307 |
| 2014/0159712 | A1 | 6/2014 | Graziani |
| 2014/0306698 | A1 | 10/2014 | Bontus |
| 2015/0008910 | A1 | 1/2015 | Goodwill |
| 2015/0276902 | A1 | 10/2015 | Weaver |
| 2015/0289939 | A1* | 10/2015 | Rahmer ............... A61B 5/0515 600/409 |
| 2015/0300987 | A1* | 10/2015 | Rahmer ............... A61B 5/7203 324/239 |
| 2015/0316628 | A1* | 11/2015 | Heidenreich ........ A61B 5/0035 324/318 |
| 2016/0354495 | A1 | 12/2016 | Harmer |
| 2018/0017639 | A1 | 1/2018 | Goodwill |
| 2018/0017641 | A1 | 1/2018 | Goodwill |
| 2018/0335487 | A1* | 11/2018 | Tonyushkin ......... A61B 5/0515 |

FOREIGN PATENT DOCUMENTS

| | | |
|---|---|---|
| WO | 1996031790 | 10/1996 |
| WO | 1997048990 | 12/1997 |
| WO | 1998013708 | 4/1998 |
| WO | 1998015851 | 4/1998 |
| WO | 1999009436 | 2/1999 |
| WO | 1999048044 | 9/1999 |
| WO | 2000010123 | 2/2000 |
| WO | 2004091395 | 10/2004 |
| WO | 2008099331 | 8/2008 |
| WO | 2010008478 | 1/2010 |
| WO | 2011010243 | 1/2011 |
| WO | 2011116229 | 9/2011 |

OTHER PUBLICATIONS

EP App. No. 16173404.1; European Search Report and Written Opinion dated Jan. 25, 2017.

Gleich et al., Tomographic imaging using the nonlinear response of magnetic particles, Nature, 435(7046): 1214-7, Jun 2005.

Goodwill and Conolly; Multidimensional x-space Magnetic Particle imaging, IEEE Transactions on Medical Imaging, 30(9): (2011) 1581-1590, ISSN 1558-254X.

Goodwill, Narrowband and x-Space Magnetic Particle Imaging, dissertation, 2010.

Knopp et al., Trajectory analysis for magnetic particle imaging, Dec. 2008, p. 386.

Konkle, J J et al.; "Twenty-fold acceleration of 3D projection reconstruction MPI", Biomedizinische Technik Walter De Gruyter Germany, vol. 58. No. 6. , Dec. 2013 (Dec. 2013), pp. 565-576, XP002773942, ISSN: 0013-5585.

Kovács, Attila, "Scanning strategies for imaging arrays," Proc. SPIE 7020, Millimeter and Submillimeter Detectors and Instrumentation for Astronomy IV, 702007 (Jul. 18, 2008); doi: 10.1117/12.790272.

PCT App. No, PCT/US2009/003764; Preliminary Report on Patentability Chapter I dated Jan. 5, 2011.

PCT App. No. PCT/US2009/003764; International Search Report and Written Opinion dated Jan. 15, 2010.

PCT App. No. PCT/US2011/028879; International Search Report and Written Opinion dated Oct. 19, 2011.

PCT App. No. PCT/US2011/028879; Preliminary Report on Patentability Chapter I dated Sep. 18, 2012.

PCT App. No. PCT/US2017/041783; International Search Report and Written Opinion dated Nov. 21, 2017.

PCT App. No. PCT/US2017/041792; International Search Report and Written Opinion dated Oct. 16, 2017.

Weber, Matthias et al.; "MPI with a mechanically rotated FFL", 2015 5TH International Workshop on Magnetic Particle Imaging (IWMPI), IEEE, Mar. 26, 2015 (Mar. 26, 2015), p. 1, XP032776021, DOI: 10.1109/IWMPI.2015.7107026, ISBN: 978-1-4799-7269-2.

Crossfield, Mike., "Have null, will fly," Mike Crossfield describes a novel approach to low-cost data tagging. IEE Review. (Jan. 2001), pp. 31-34.

Karsten, Robert P., "The Use of Flying Null Technology in the Tracking of Labware in Laboratory Automation." Downloaded from jla.sagepub.com, at Univ California Berkeley Lib, Jun. 16, 2015.

Sparavigna, Amelia. "Labels discover physics: the development of new labelling methods as a promising research field for applied physics." Dipartimento di Fisica, Politecnico di Torino. Corso Duca degli Abruzzi 24, Torino, Italy, pp. 1-16.

Office Action dated Nov. 27, 2018 for U.S. Appl. No. 15/648,421 (pp. 1-7).

Office Action dated Mar. 8, 2019 for U.S. Appl. No. 15/648,401 (pp. 1-8).

* cited by examiner

Front View (solid section in Fig. 3)

Top View (dashed section in Fig. 3)

MAGNETIC PARTICLE IMAGING

CROSS-REFERENCE TO RELATED APPLICATIONS

The current application claims priority under 35 U.S.C. § 119 to U.S. Provisional Patent Application No. 62/361,463 filed Jul. 12, 2016 and entitled "MAGNETIC PARTICLE IMAGING," and to U.S. Provisional Patent Application No. 62/361,475 filed Jul. 12, 2016 and entitled "MAGNETIC PARTICLE IMAGING," the contents of each are hereby incorporated by reference in its entirety.

STATEMENT REGARDING FEDERALLY SPONSORED RESEARCH OR DEVELOPMENT

This invention was made with government support under grant numbers 1R43DA041814, 1R43EB020463, and 5R01EB013689 awarded by the National Institutes of Health. The government has certain rights in the invention.

BACKGROUND

Magnetic particle imaging (MPI) is a technique allowing for the detection of certain nanoparticles and may be used, for example, in diagnostic imaging applications. Imaging may be facilitated through magnets designed to create a Field-Free Region (FFR). Examples of field free regions include a Field Free Point (FFP) and a Field Free Line (FFL).

SUMMARY

A Magnetic Particle Imaging (MPI) system is disclosed. Implementations may include a magnet configured to generate a magnetic field having a field free line within the magnetic field, the field free line having an axis and a center. A first shim magnet may be positioned above the field free line and configured to modify the magnetic field.

In some variations, a second shim magnet can be positioned below the field free line. The second shim magnet can be configured to modify the magnetic field. The first shim magnet can be a passive shim, an active shim, or an angled shim magnet pointed generally toward the field-free line, or elongate.

In other variations, the first shim magnet can configured to decrease a gradient along the axis of the field-free line or improve the fidelity of the field-free line.

In yet other variations, the magnet does not include a flux return or can include a flux return integrated with the magnet where the first shim magnet may not require water cooling. The first shim magnet can be configured to reshape the field free line to approximate an ellipsoidal field-free region or can be configured for slab imaging.

In other variations, the first shim magnet can be configured to be actively controlled to counteract field free line fidelity degradation resulting from gradient strength changes. The first shim magnet can also be configured to be actively controlled to counteract field free line fidelity degradation resulting from shifting of the field free line during imaging.

In some variations, a control system can be configured for imaging while avoiding excitation of a particular portion of a subject. The control system can be configured for increased spatial selectivity in hybrid imaging and magnetic actuation MPI.

In yet other variations, a shim magnet can be configured to provide localized heating and energy deposition in three dimensions when the magnetic particle imaging system is configured for spatially-selective magnetic fluid hyperthermia applications.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

An MPI system can be used to image tracer particles that may be present in an object, for example, in the anatomy of a person or animal. An MPI system can image tracer particles by causing them to emit electromagnetic radiation in response to a locally changing magnetic field. The change in the magnetic field can result from changes in an externally applied magnetic field, from movement of the tracer particles, or a combination of the two.

In many implementations, an MPI system will produce magnetic fields that include a field-free region or magnetic null. Tracer particles present in an object can change the orientation of their magnetic moment as they pass through such a region, or such a region passes through them, and the magnetic field experienced by the tracer particles changes from being oriented in a one direction to being oriented in another direction.

MPI systems typically include a detector configured to detect the electromagnetic radiation from tracer particles, or detect the changes in magnetic flux resulting the tracer particles responding to changes in the magnetic field or moving through the magnetic field. This electromagnetic signal can be used to generate an image of the tracer particles located within an imaging volume.

Some implementations of magnetic particle imaging can include moving the object to be imaged, moving the location of the field-free region, or a combination of the two.

The distribution of tracer particles imaged in a subject can be related to particular anatomical features or physical structures of the object (e.g., particles accumulated in a cavity or blood vessel) or to a distribution of elements in the object that the tracer particles have attached to (e.g., a particular molecule, cell or tissue type that has a propensity to preferentially bond with the tracer particles or molecules that the tracer particles have been attached to or contained within). In this way, the determined location of the tracer particles can be used to image features inside the object.

Figure 1:
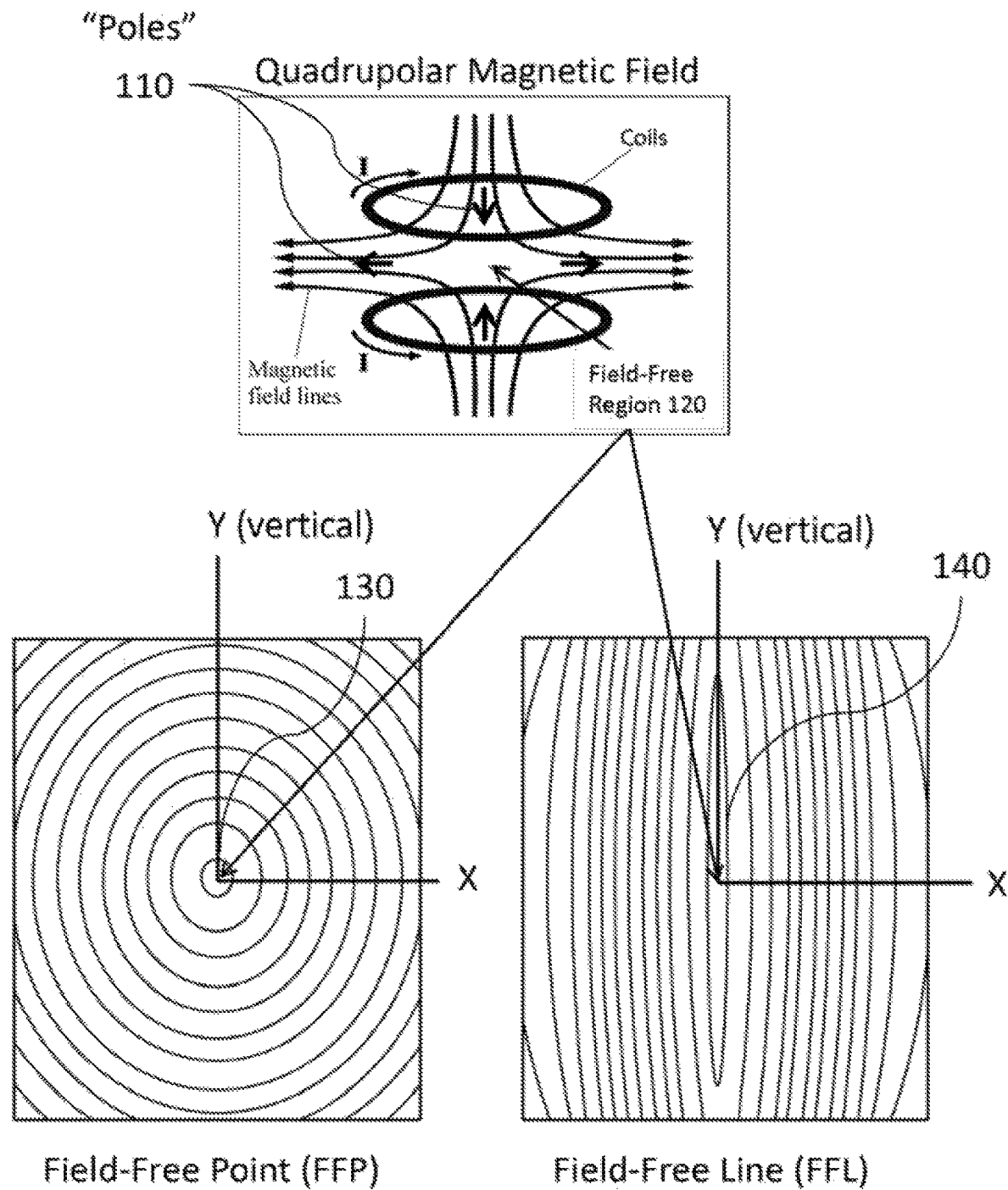
FIG. 1 is a diagram illustrating a quadrupolar magnetic field, a FFP, and a FFL in accordance with certain aspects of the present disclosure.

FIG. 1 is a diagram illustrating a quadrupolar magnetic field, a FFP 130, and a FFL 140, in accordance with certain aspects of the present disclosure. An MPI system can produce a quadrupolar magnetic field (upper part of FIG. 1) that contains a magnetic null, zero-point or field-free region 120. In the simplified example of FIG. 1, two coils with currents traveling in opposite directions are generating a quadrupolar magnetic field. The four "poles" 110 of the quadrupolar magnetic field are shown by the short arrows. The poles 110 are provided as examples of a magnetic configuration equivalent to the two opposed coils shown in FIG. 1. The poles 110 are located at points of symmetry between the two coils in the case where the currents in the coils are equal and opposite.

In some implementations, the field-free region 120 can be a FFP 130 (as shown by the simplified illustration in the lower left half of FIG. 1). In other implementations, the field-free region can take the form of a field free line 140 (as shown by the simplified illustration in the lower right half of FIG. 1). The Y-axis of the plots in FIG. 1 are labeled as vertical to be consistent with later figures, showing the typically vertical orientation of field-free line 140. When an MPI system is configured to generate a field-free line 140, the MPI signal is received from the line, instead of from a point. FFL configurations may thus utilize projection-based imaging and reconstruction techniques.

Field-free line 140 is a generally elongate region, having a length and a thickness, where the magnetic field is significantly lower than at other locations in the magnetic field generated by the MPI system. As used herein, a "field-free line" is understood to account for the reality that the line may not be perfectly straight, nor completely absent magnetic field, but that such is generally the goal of an FFL.

The field-free line 140 can, in some implementations, be generally elongate or "linear" only within an imaging volume of the MPI system. It is less important for the FFL to maintain linearity outside the imaging volume and thus field-free line 140 may deviate to a different shape away from its center, proximate the center of the imaging volume. Similarly, as used herein, a "field-free point" refers to an approximately spherical region of low magnetic field.

Figure 2:
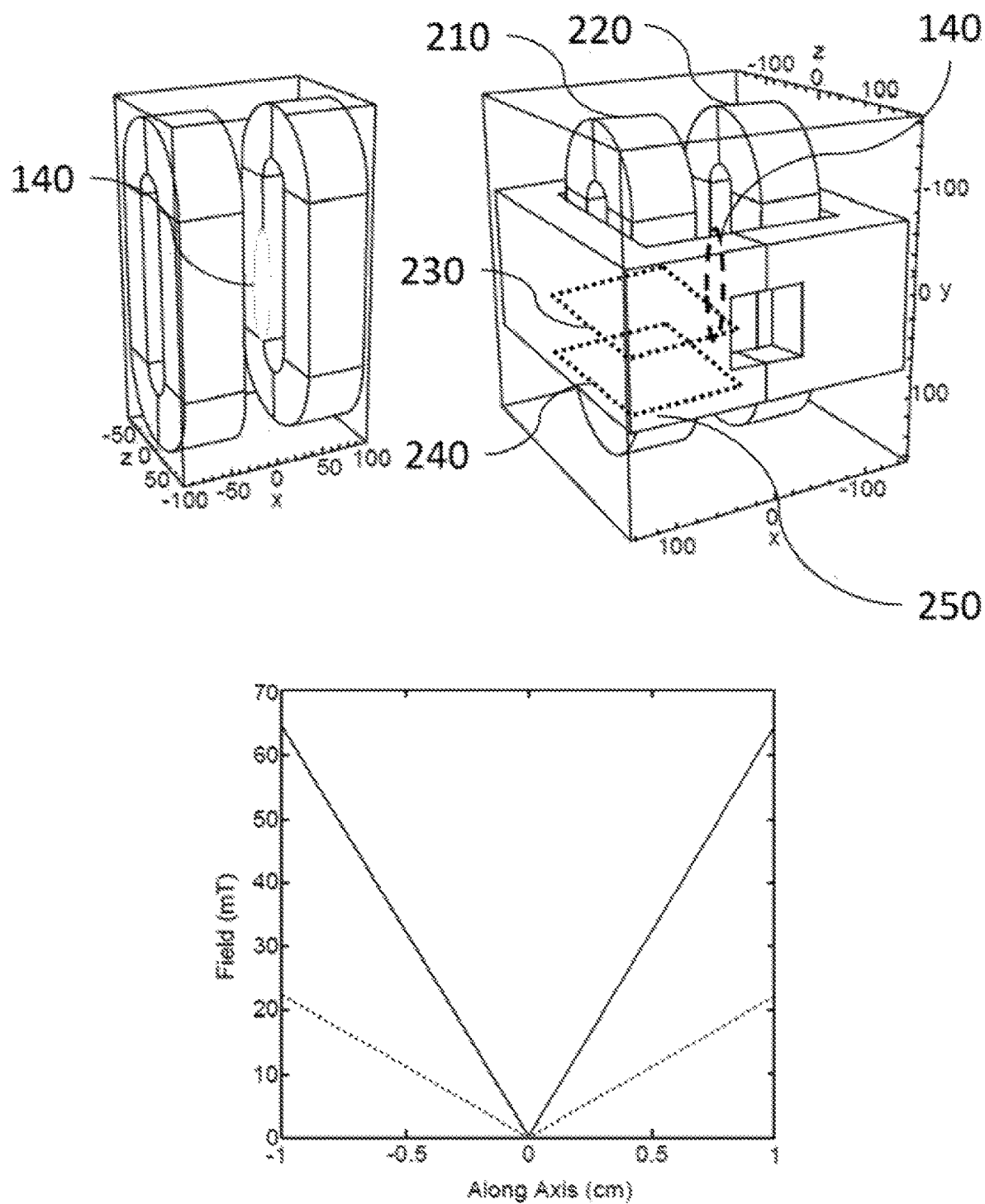
FIG. 2 is a diagram illustrating a simplified MPI system and FFL, a simplified MPI system with a flux return, and two simplified magnetic flux paths shown with an exemplary increase in magnetic field gradient due to the flux return in accordance with certain aspects of the present disclosure.

FIG. 2 is a diagram illustrating a simplified MPI system with FFL 140 in the upper left corner. In the upper right corner, FIG. 2 illustrates an MPI system with a flux return 250 and two simplified magnetic flux paths 230 and 240. The bottom of FIG. 2 includes a graph detailing an exemplary increase in magnetic field gradient due to the inclusion of flux return 250 in accordance with certain aspects of the present disclosure.

As shown in FIG. 2, the MPI system can include a magnet configured to generate a magnetic field that has a field-free line 140 within the magnetic field. In the exemplary design shown in FIG. 2, the magnet includes a first magnet 210 and a second magnet 220. The present disclosure, however, contemplates that the requisite magnetic field and field free line may be generated by any number, and any type, of magnets. For example, the magnet may incorporate multiple magnets (2, 3, 4, etc.) and such magnets can be, for example, a permanent magnet, a current-carrying coil or electromagnet, an electromagnet with a flux return, or any combination of such magnets. The magnet may in fact be only a single magnet, to the extent such is capable of generating a field free line (for example, a Halbach cylinder). The discussion of the exemplary magnet design herein including two main magnets is not intended to be limiting.

Field-free line 140 is understood to have an axis extending along the length of field-free line 140 and a center on the axis, which is generally understood to be proximate the center of the imaging volume.

The upper right corner of FIG. 2 shows a flux return 250 integrated with the magnet (here illustrated as including first and second magnets 210 and 220). As used in this disclosure, "flux return" refers to any arrangement of material components that shape the magnetic flux. Flux return 250 may contain, for example, a ferromagnetic material such as iron (or any other material having a low reluctance as compared to other substances or as compared to air), to more effectively channel, guide, shape, or concentrate magnetic flux. Flux return 250 may be fabricated, for example, in two separate halves, or in a number of layers of laminates that can be stacked or otherwise assembled to form flux return 250.

Flux returns of the present disclosure can shape magnetic flux distributions by way of, for example, creating flux paths of varying reluctance. For example, a path including a large amount of iron compared to air will have a lower reluctance than a same-length path with less iron and more air. Magnetic resistance, magnetic reluctance, or "reluctance" as used herein, is a concept used in the analysis of magnetic circuits. It is analogous to resistance in an electrical circuit. In likeness to the way an electric field causes an electric current to follow the path of least resistance, a magnetic field causes magnetic flux to follow the path of least magnetic reluctance. It is a scalar, extensive quantity, akin to electrical resistance. The unit for magnetic reluctance is inverse Henry, $H^{-1}$.

As shown at the bottom of FIG. 2, the flux guiding and concentrating effect of a flux return can be leveraged to create larger field gradients, in which a stronger field is obtained using a flux return 250 as opposed to a magnet system without a flux return. The graph at the bottom of FIG. 2 illustrates the increased gradient in the magnetic field when a flux return is utilized.

Field symmetry and fidelity can be described as how well the field realized by a magnet arrangement matches a desired shape and flux density, e.g., a symmetric FFL 140. As used herein, "magnetic field fidelity" or "field fidelity" refers to the quality of the magnetic field pattern as it relates to, for example, the shape and quality of FFL 140. For example, it may be beneficial to have a highly linear and symmetric FFL 140, with low gradient along the axis of the FFL 140, but with high field gradients in the directions orthogonal to the axis surrounding FFL 140.

Figure 3:
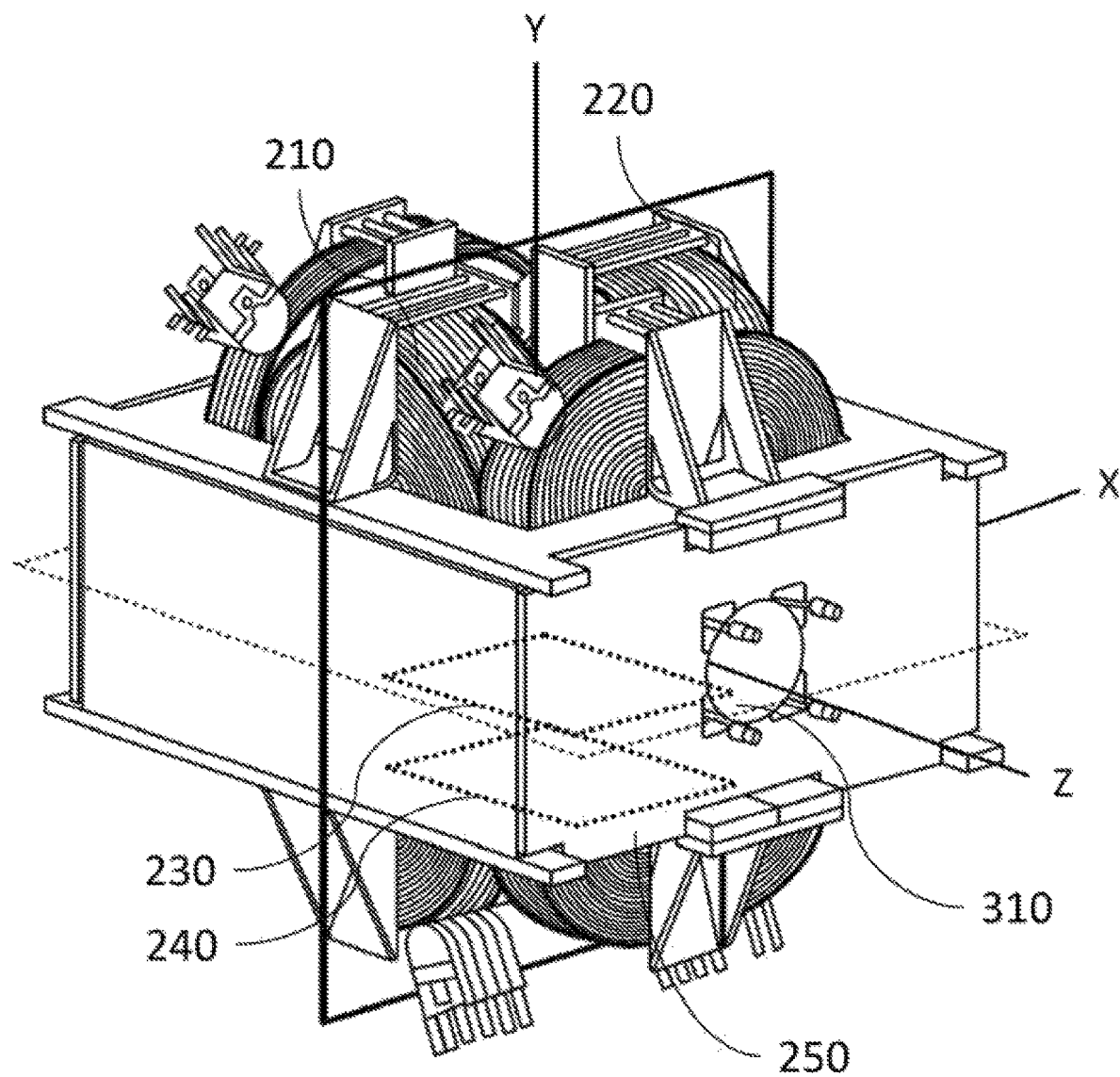
FIG. 3 is a perspective diagram illustrating an exemplary magnet configuration for an MPI system including a flux return in accordance with certain aspects of the present disclosure.

In one implementation of an MPI system consistent with the present disclosure, illustrated in FIG. 3, the assembly includes four high-powered, water-cooled electromagnets where the magnets are elongate (i.e., longer in one dimension than another and not circular). FIG. 3 also illustrates an exemplary flux return 250 in accordance with certain aspects of the present disclosure.

Figure 5:
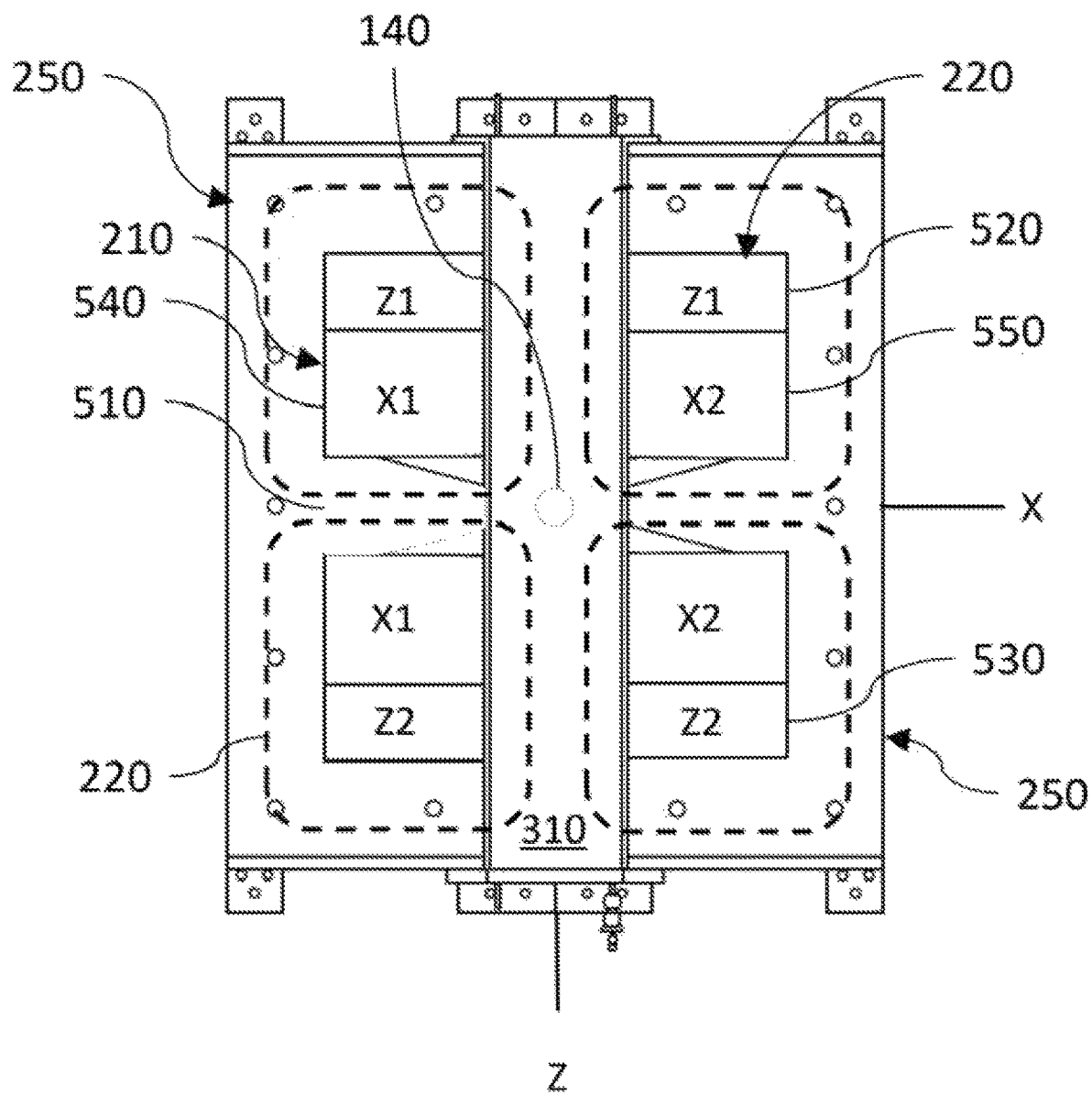
FIG. 5 is a top sectional diagram of the MPI system of FIG. 3 illustrating a flux return that includes a pole piece in accordance with certain aspects of the present disclosure.

In some implementations, two of the magnets may be configured to generate a homogenous field for shifting the position of FFL 140, for example, along the Z axis; such magnets may be referred to herein as "shifting magnets" and are labeled Z1 and Z2 (see, e.g., FIG. 5). Main magnets, labeled herein as X1 and X2 (see FIG. 5), may also be configured to alter the magnetic field in a manner to shift the location of FFL 140. In other implementations, additional magnets can be used to generate a fast drive field that acts to rapidly shift the mean position of FFL 140.

As shown in FIG. 3, the MPI system can also include a bore 310 to receive a subject to be imaged. The FFL 140 can extend perpendicularly to the bore 310. In some implementations, the MPI system can be configured to rotate about the axis of the bore 310, and in such implementations, the orientation of the magnetic fields and FFL 140 changes correspondingly.

Figure 4:
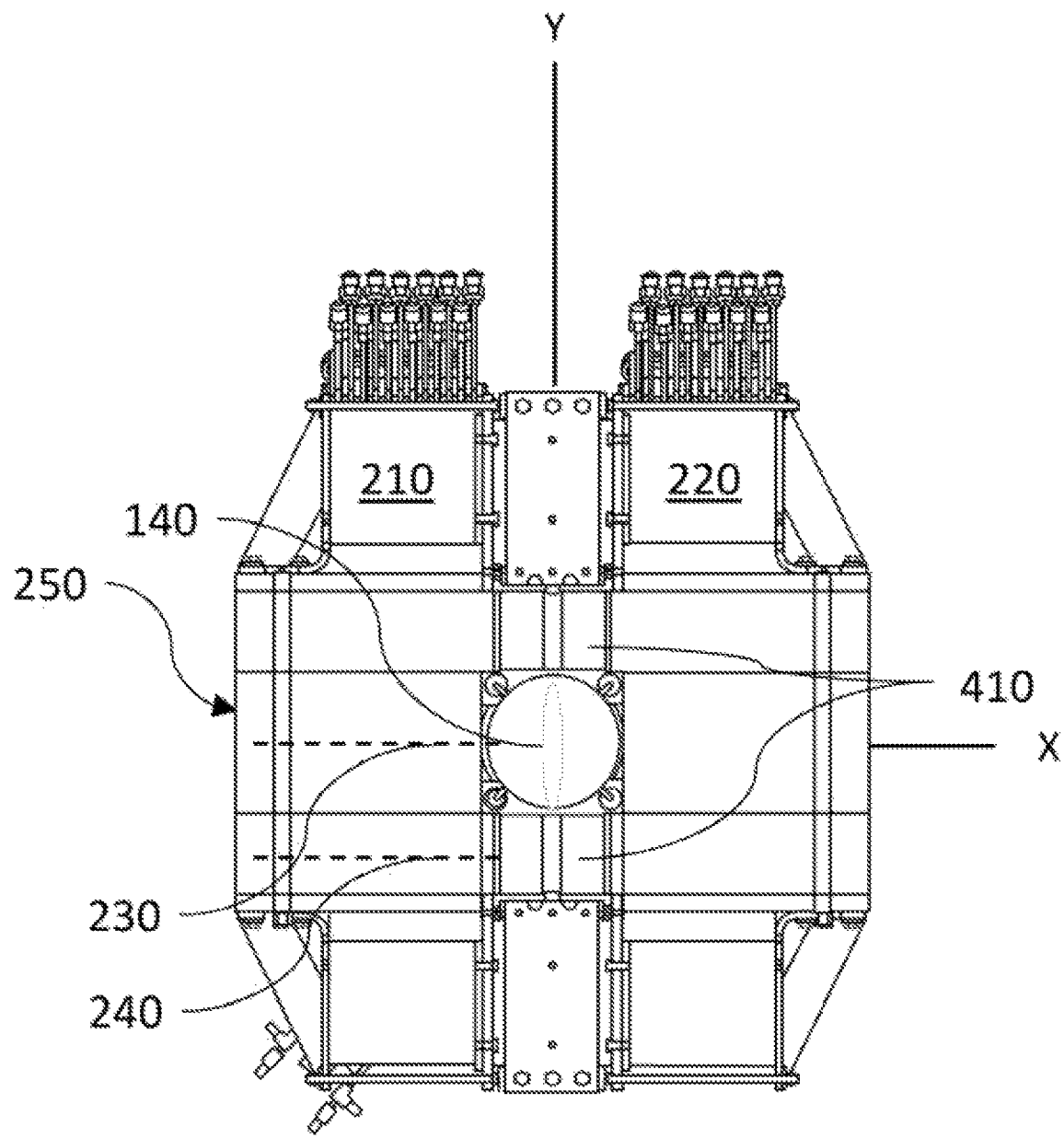
FIG. 4 is a front sectional diagram of the MPI system of FIG. 3 illustrating a field free line and two magnetic flux paths in accordance with certain aspects of the present disclosure.

FIG. 4 is a sectional view of the MPI system of FIG. 3 (denoted by the heavy solid section line in FIG. 3, shown through the middle of the system, and corresponding to the X-Y plane in that figure). FIG. 4 illustrates a flux return 250, which, in this particular embodiment, surrounds the four magnets. Also shown is FFL 140 and two magnetic flux paths 230 and 240 in accordance with certain aspects of the present disclosure.

FIG. 5 is another sectional view of the MPI system of FIG. 3 (denoted by the dashed line around the system in FIG. 3, corresponding to the X-Z plane in that figure). FIG. 5 also illustrates flux return 250 and shows its included pole pieces in accordance with certain aspects of the present disclosure. A pole piece 510 (one shown in cross-hatch for illustrative purposes) can pass through the center of, for example, main magnets 210, 220, which are shown in FIG. 5 as X1 and X2.

In an exemplary embodiment, flux return 250 may be configured such that a first magnetic flux path 230 at approximately the center of field-free line 140 has a first reluctance, and a second magnetic flux path 240 distal from the center of field-free line 140 has a second reluctance— and the second reluctance is lower than the first reluctance (see simplified illustrations of flux paths 230 and 240 shown as dashed lines in FIGS. 3 and 4). In this embodiment, it is contemplated that the second magnetic flux path 240 "distal from the center of the field-free line 140," has a lower reluctance by virtue of the design of flux return 250—and not by flux path 240 simply traveling a shorter distance (that is also at a point distal from the center of FFL 140). In the description of this embodiment, it is assumed that magnetic flux paths 230 and 240 are each paths that extend out to pass through a point adjacent field free line 140.

Figure 6:
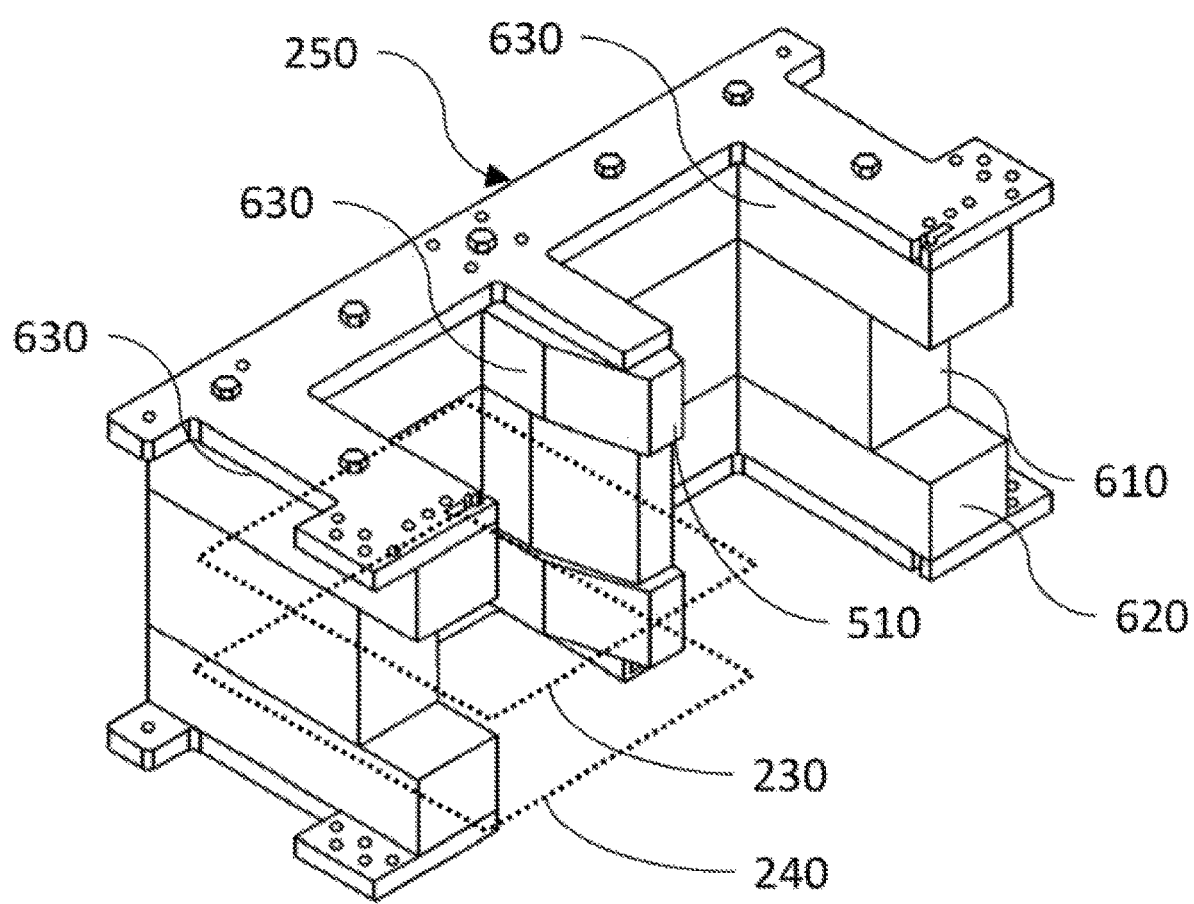
FIG. 6 is a perspective diagram of an exemplary flux return in accordance with certain aspects of the present disclosure.
Figure 7:
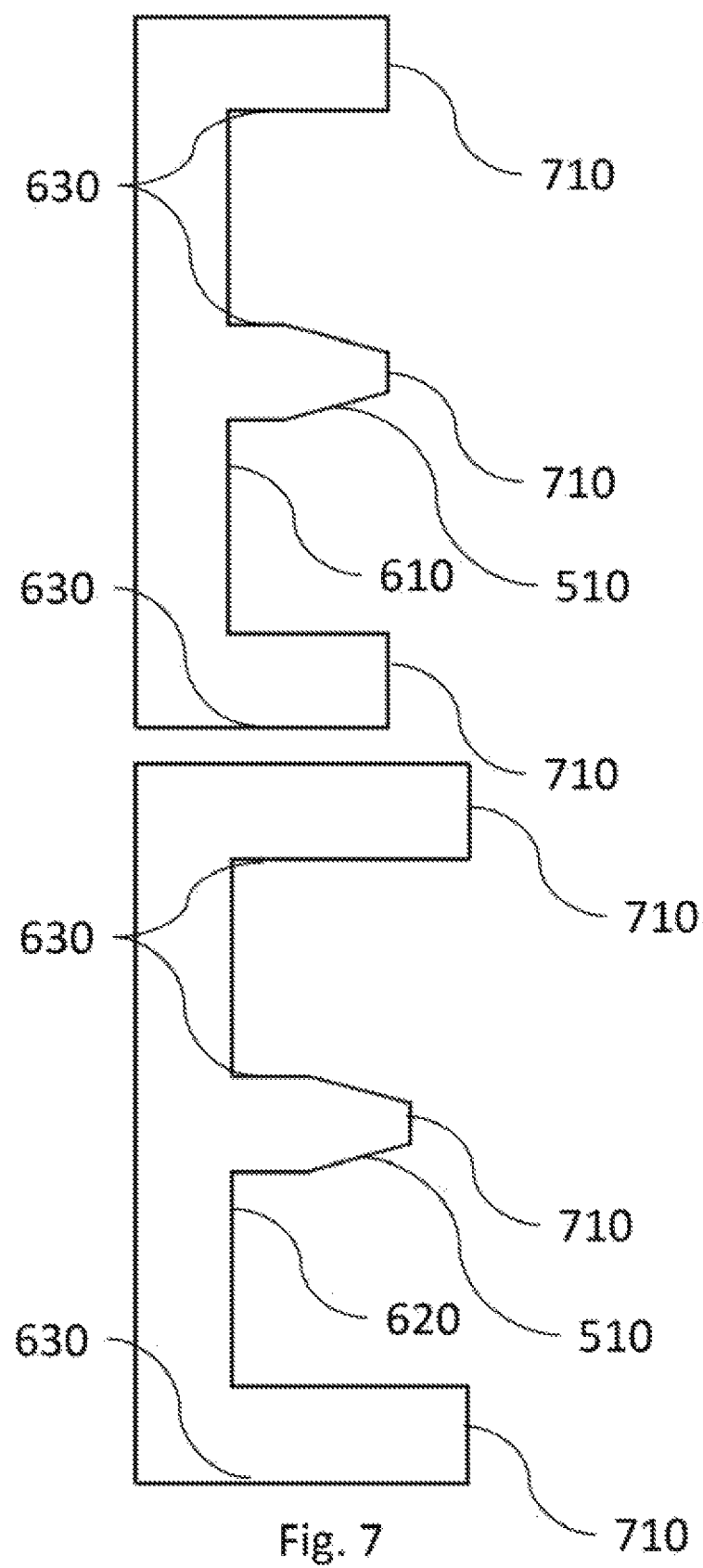
FIG. 7 is a simplified diagram of two exemplary laminates that form the flux return of FIG. 6 in accordance with certain aspects of the present disclosure.

FIG. 6 illustrates one implementation of this exemplary embodiment, through a perspective view of an exemplary flux return 250, while FIG. 7 shows two of the three laminates that make up the flux return of FIG. 6.

As shown in FIGS. 6 and 7, flux return 250 can include a pole piece 510 having an end, and that end can include a step. To form the step, flux return 250 may include laminations or layers, where a first lamination 610 and a second lamination 620 form the step. In this example, first magnetic flux path 230 passes through first lamination 610 and second magnetic flux path 240 passes through second lamination 620. As shown, the step in pole piece 510 is configured such that the bottom laminate 620 protrudes farther toward the imaging volume than the laminate 610 at the center of pole piece 510, thereby increasing the amount of flux return material (e.g., iron) in the bottom portion of the pole piece and thus decreasing the reluctance at points distal from the center of FFL 140. While this reluctance-altering design is shown as creating steps through the use of different shaped laminates, it may also be created by a single pole piece, machined to similar specifications—or by a combination of laminate(s) and machined pole piece(s). While this implementation of steps has been shown in relation to pole piece 510, it is contemplated that similar steps on the outer portions of flux return 250 (e.g., in the vicinity of labels 610 and 620) may be implemented.

While the reluctance varying properties described above may be created through "steps," for example in pole piece 510 as described, these properties may also be achieved by machining a pole piece to create a more smoothly varying flux return pole profile. For example, pole piece 510 may be machined in a continuous or partial curve that likewise results in points distal from the center of FFL 140 protruding further toward the imaging volume. Smoothly varying pole pieces may take the shape of an arc or chord, a parabolic, hyperbolic, or hyperbolic tangent shape, for example. In yet other implementations, there can be any number of laminates or layers of pole pieces of varying length that can be stacked in order to form a semi-smooth or fine-stepped pole piece.

In yet another implementation, the second reluctance may be lower than the first reluctance at least partially by virtue of flux return 250 including a lower reluctance material in the vicinity of the second magnetic flux path 240 than the reluctance of the material in the vicinity of the first magnetic flux path 230.

In still other implementations, the second reluctance can be lower than the first reluctance by virtue of the shape of the flux return in combination with chosen flux return materials.

Flux return 250 can include "flux return arms" (for example, shown as 630 in FIG. 6) that can also play a role in shaping or concentrating magnetic flux, apart from the role that pole piece 510 may play.

Figure 8:
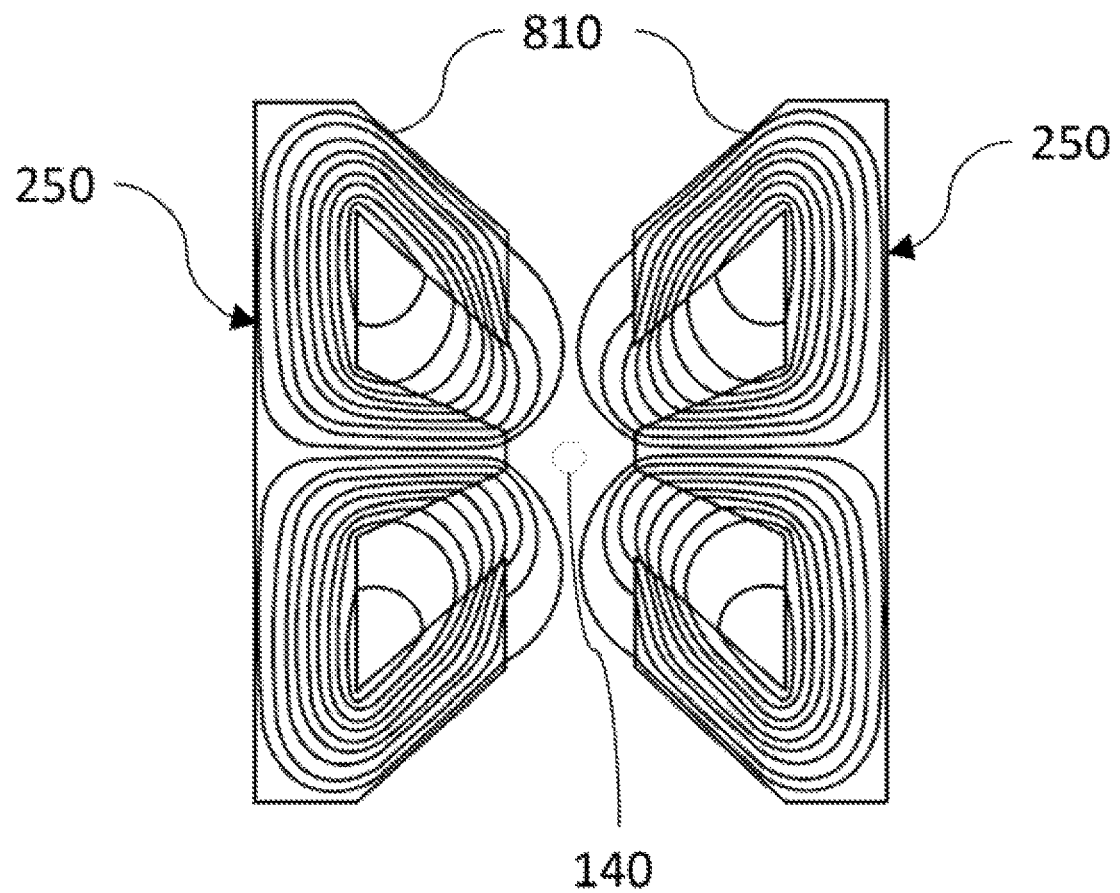
FIG. 8 is a simplified diagram of an exemplary flux return that includes angled arms in accordance with certain aspects of the present disclosure.

FIG. 8 is a simplified diagram of an exemplary flux return 250 that includes angled flux return arms 810 in accordance with certain aspects of the present disclosure. As shown in FIG. 8, a flux return arm can be angled toward the field free line at the imaging volume. This angling is distinct from flux return arms 710 that are oriented generally perpendicular to the axis of bore 310, as shown in FIGS. 6 and 7. Such angled flux return arms can further focus or shape the magnetic flux in the region of FFL 140 at the imaging volume location. FIG. 8 also illustrates magnetic field lines that may result from such angled flux return arms.

Another manner in which the magnetic flux density can be shaped or optimized for MPI is illustrated in, e.g., FIGS. 6 and 7, wherein pole piece 510 can be fabricated in a manner that includes a taper. Such a taper in pole piece 510 can increase a magnetic flux density near the taper and proximate the field-free line 140.

The taper referred to herein is (as shown in the figures) tapered transverse to the FFL 140 or, in other words, the outer edges of pole 510 are tapered towards FFL 140. The taper may be linear as shown, or can be smoothly varying over part or all of its cross-section (or may be a combination of smoothly varying and linear sections). The taper can come to a point at the end of pole piece 510, or can be only a partial taper that terminates in a flat end of pole piece 510 (as shown in the exemplary drawings). The taper can be accomplished by any combination of machining or the application of different sized layers of material making up pole piece 510 or flux return 250.

Magnetic fields in an MPI system can be modified or further shaped through shimming. For example, shimming may be performed to shape magnetic fields to improve the fidelity of field free line 140 or to change the shape of field free line 140.

Passive shimming refers to the mechanical attachment of permanent magnets or other magnetic materials (e.g., iron, steel, mu-metal, etc.) to the MPI system in order to shape the magnetic field. Some implementations include adding passive shim sets to optimize the magnetic field at particular specific operating points or strengths of the main gradient magnet. Such passive shim sets will often sufficiently optimize magnetic field distribution over a significant range of gradient field strengths (e.g., 4-7 T/m). However, when a gradient operating point outside of the optimized range is desired, a separate set of passive shims may need to be utilized.

Active shimming refers to the powering of electromagnets included within the MPI system in order to shape the magnetic field, often in a manner where the power driving a shim magnet is actively changed during operation of the magnetic particle imaging system.

The shimming of an MPI system may be performed utilizing active shims, passive shims, or a combination of both.

Figure 9:
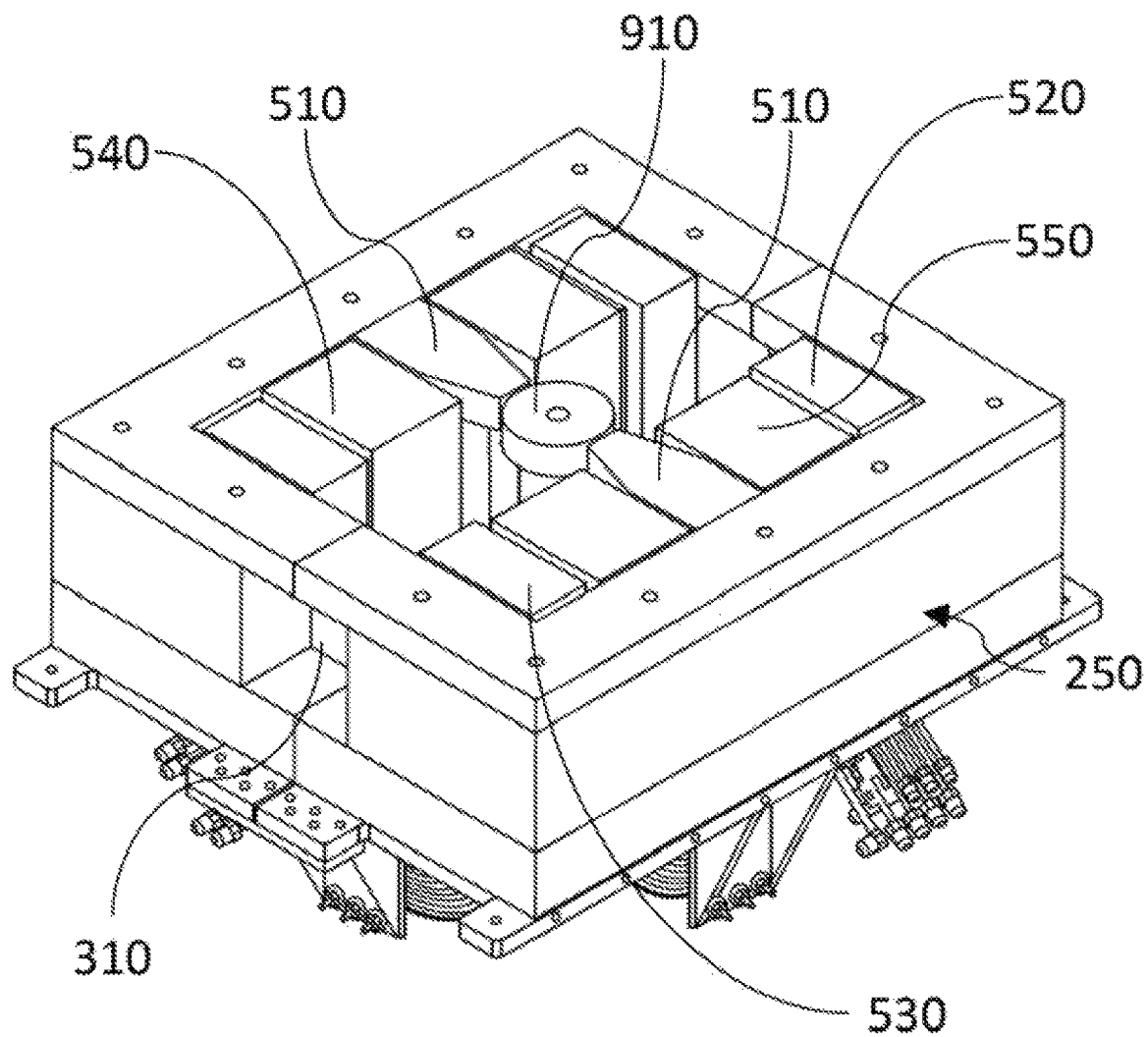
FIG. 9 is a perspective diagram of an exemplary MPI system illustrating an example of a shim magnet in accordance with certain aspects of the present disclosure.
Figure 10:
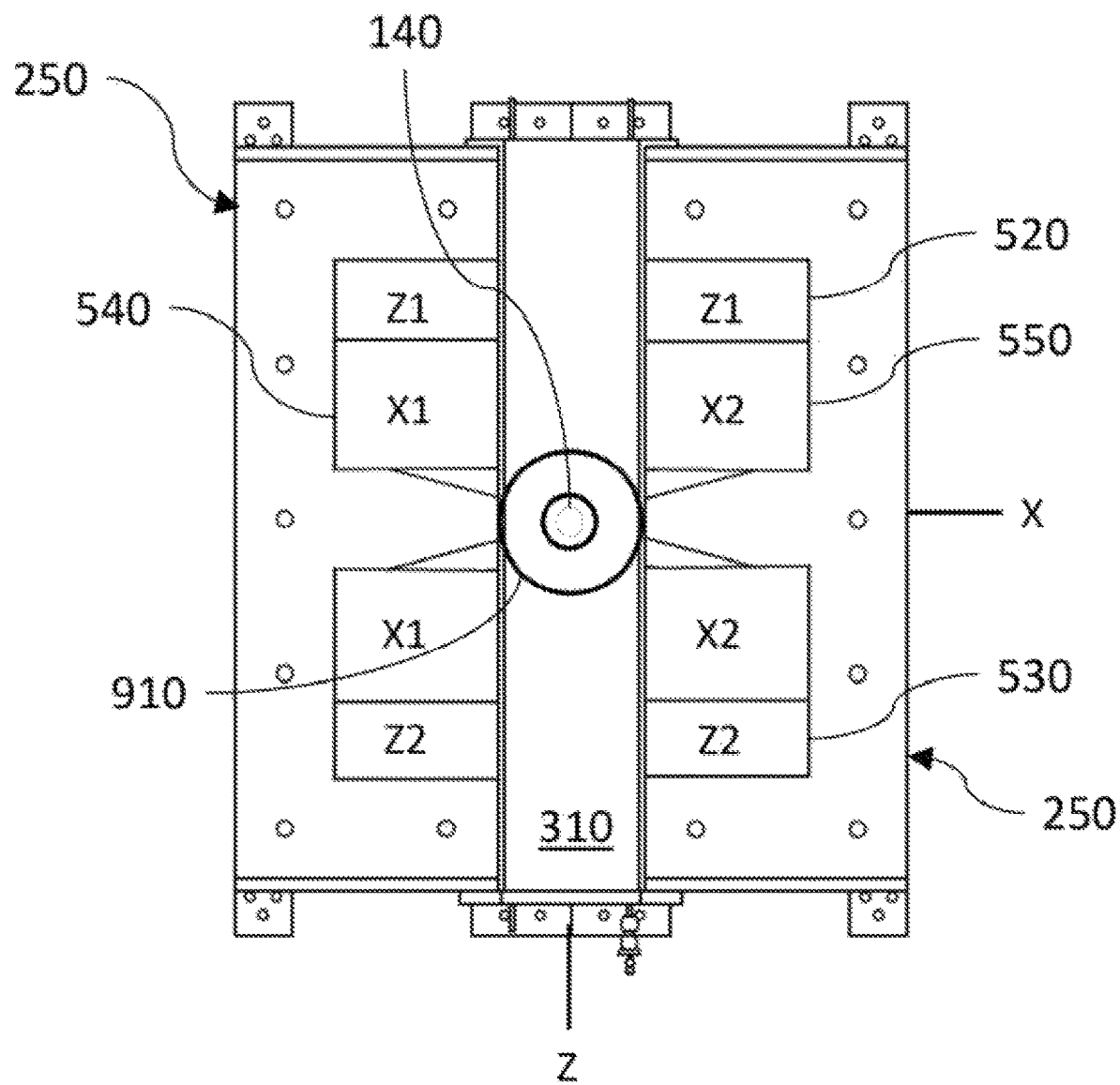
FIG. 10 is a top sectional diagram of the MPI system of FIG. 9 illustrating an example of a shim magnet in accordance with certain aspects of the present disclosure.

FIG. 9 is a perspective diagram of an exemplary MPI system illustrating an example of a shim magnet 910 in accordance with certain aspects of the present disclosure. FIG. 10 is a top sectional diagram of the MPI system, and FIG. 11 is a side sectional diagram of the MPI system.

As shown in FIG. 9, a shim magnet 910 may be centered along the length of bore 310, may be aligned essentially in the center of flux return 250, and may be positioned between pole pieces 510. As can be seen in FIG. 11, in this location, shim magnet 910 is approximately centered above the portion of field free line 140 that is located in the imaging volume within bore 310 (referred to herein as "above the field free line"). Shim magnet 1110, also shown in FIG. 11, may similarly be placed at a position that is approximately centered below the portion of field free line 140 that is located in the imaging volume within bore 310 (referred to herein as "below the field free line"). In one particular implementation, shim magnets 910 and 1110 are centered on the axis of FFL 140 when FFL 140 is located in the center of the imaging volume (in this case, at the center of bore 310, and centered between magnets 210 and 220), thereby allowing for beneficial shaping of FFL 140, as described further below. During imaging, FFL 140 may shift to different positions within the imaging volume, and thus shim magnets 910 and 1110 would only be approximately centered above FFL 140 at such times.

Figure 11:
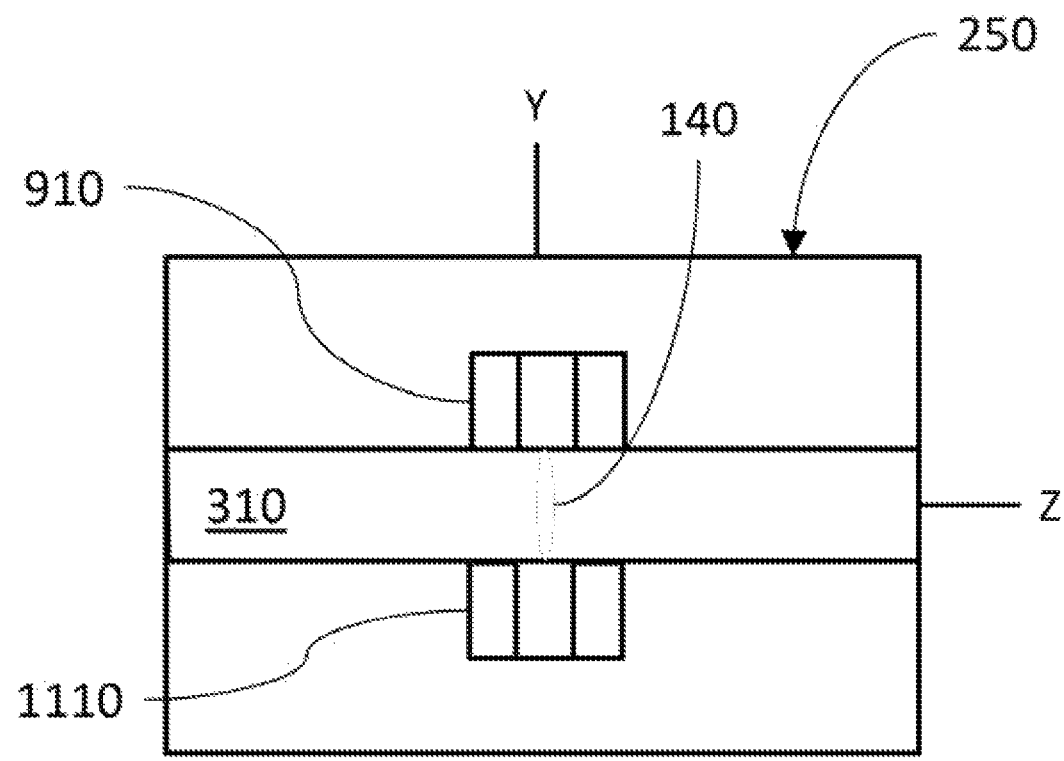
FIG. 11 is a side sectional diagram of the MPI system of FIG. 9 illustrating an example of a shim magnet in accordance with certain aspects of the present disclosure.

Although a single pair of opposed shim magnets 910, 1110 are shown in the exemplary FIGS. 9-11, the present disclosure contemplates that there can be any number of shim magnets (e.g., 1, 2, 4, 6, etc.), located at any position along bore 310, and at any azimuthal angle around bore 310 (e.g., oriented along the X-axis instead of the Y-axis as shown). In addition, active shim magnets can be electrically connected to one another in series, or parallel, or they can be completely independent of one another.

Figure 12:
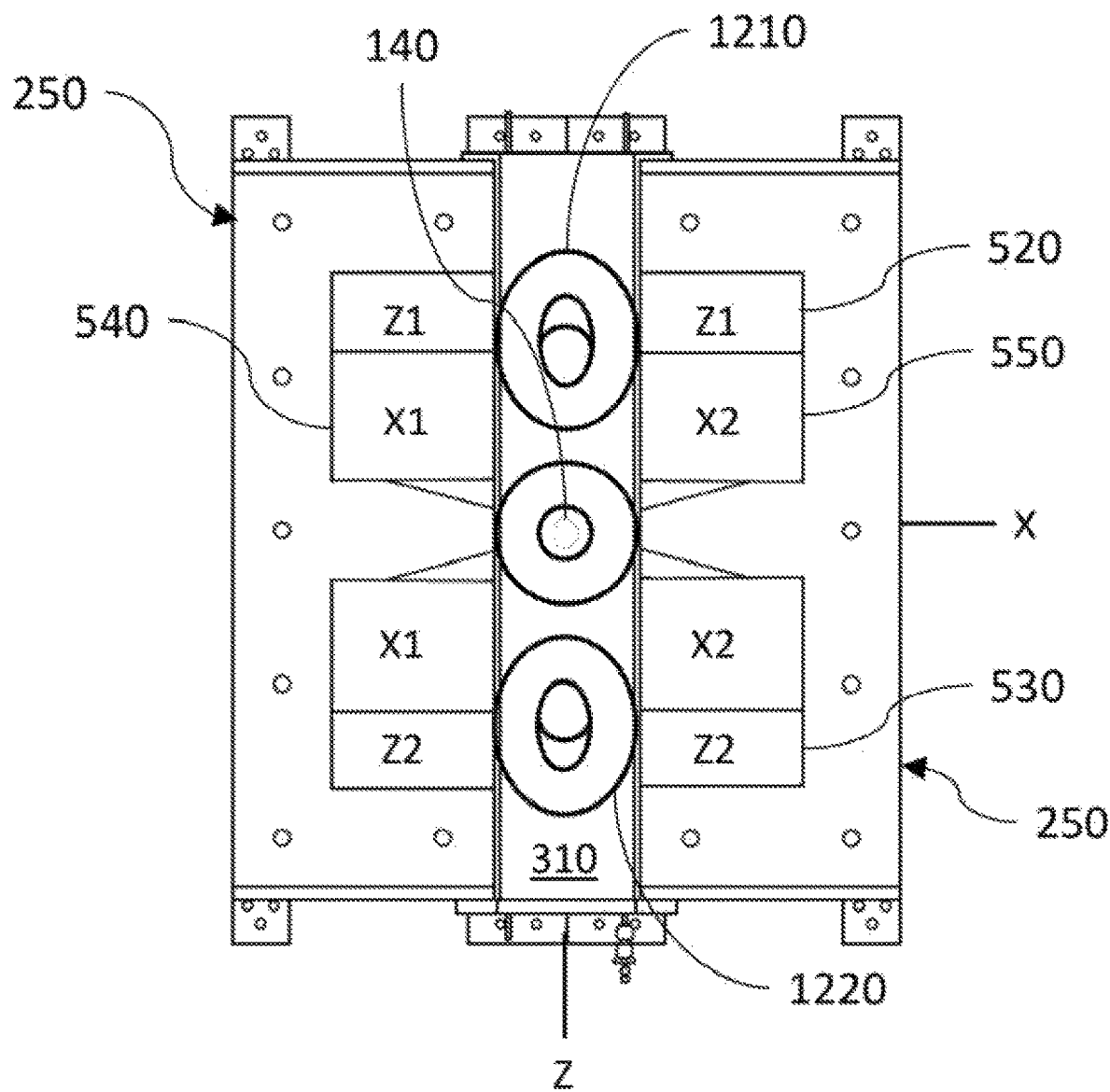
FIG. 12 is a top sectional diagram of an exemplary MPI system illustrating an example of angled shim magnets in accordance with certain aspects of the present disclosure.
Figure 13:
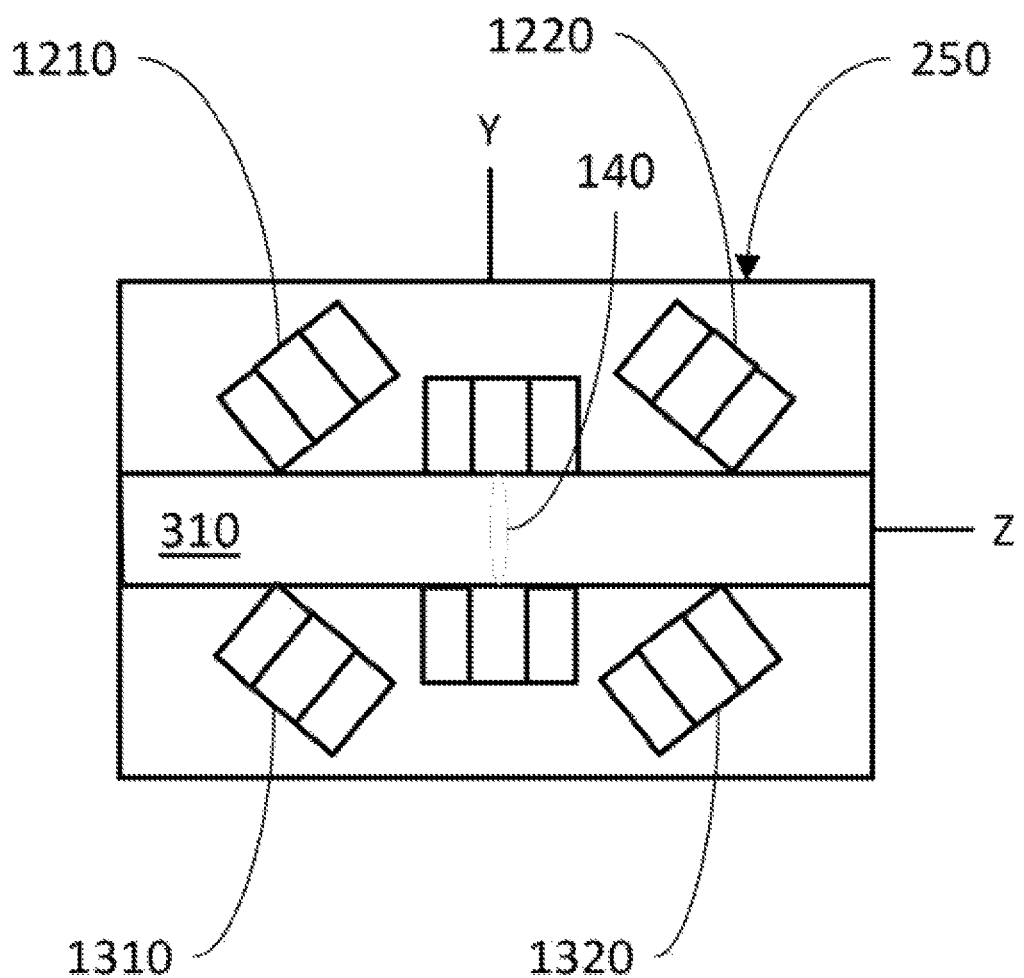
FIG. 13 is a side sectional diagram of the MPI system of FIG. 12 illustrating an example of angled shim magnets in accordance with certain aspects of the present disclosure.

FIGS. 12 and 13 illustrate alternative, angled shim magnets 1210, 1220 in accordance with certain aspects of the present disclosure. Such angled shim magnets can be used to further shape or control FFL 140 and can be located away from (i.e., not on) the axis of FFL 140, but optionally pointed generally toward FFL 140. Angled shim magnets 1210, 1220 can be arranged symmetrically such that the components of the magnetic fields generated in the Z direction can substantially cancel at the axis of FFL 140. Angled shim magnets 1210, 1220 can have any angle relative to FFL 140, for example, approximately 45 degrees as shown, 0 degrees (i.e. parallel to FFL 140), 30 degrees, 60 degrees, etc. As shown in FIG. 11, there can also be a similar arrangement of angled shim magnets 1310, 1320 below bore 310 that are opposite angled shim magnets 1210, 1220.

Figure 14:
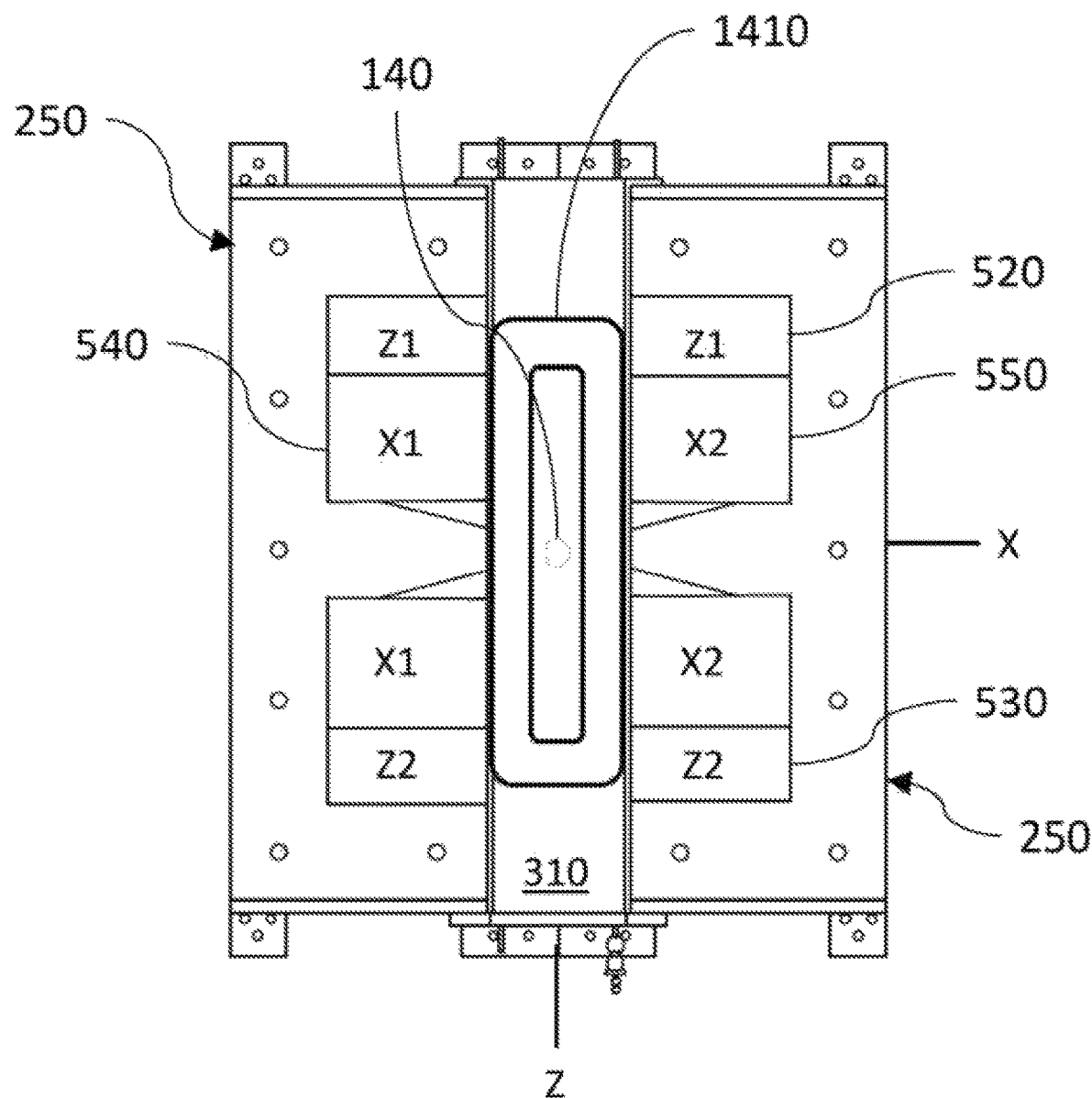
FIG. 14 is a top sectional diagram of an exemplary MPI system illustrating an example of an elongate shim magnet in accordance with certain aspects of the present disclosure.
Figure 15:
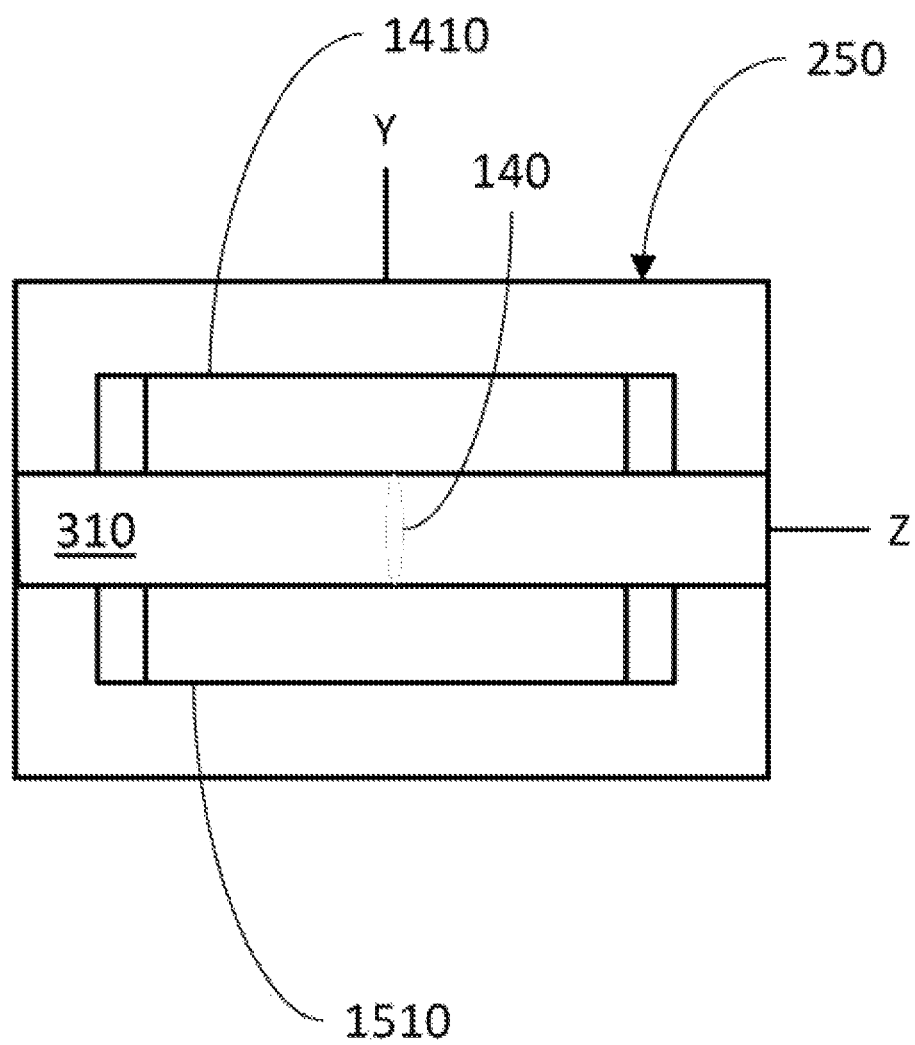
FIG. 15 is a side sectional diagram of the MPI system of FIG. 14 illustrating an example of an elongate shim magnet in accordance with certain aspects of the present disclosure.

FIG. 14 is a top sectional diagram of the MPI system illustrating an elongate shim magnet 1410 in accordance with certain aspects of the present disclosure, and FIG. 15 is a side sectional diagram also depicting elongate shim magnet 1410. Elongate shim magnet 1410 can be similar to shim magnet 910, but elongated along the length of bore 310. As shown in FIG. 15, certain embodiments may also include an opposing elongate shim magnet 1510 below bore 310.

In embodiments of the present disclosure having a shim magnet above the FFL, below the FFL, or above and below the FFL, the shim magnet(s) can be configured to aid the shaping of the magnetic flux distribution around the magnet (for example, setting up a desired flux between a pole piece 510 to a flux return arm 630). Shim magnet(s) configured in this manner can improve the fidelity of the field free line, and can result in a decrease of the gradient along the axis of the field free line. In one implementation, the shim magnet(s) can be of sufficient strength to facilitate a desired magnetic flux distribution such that the main magnet does not require a flux return. In another implementation, the flux-facilitating nature of the shim magnet(s) is utilized with a magnet and flux return design facilitating a relatively high fidelity FFL, thereby decreasing the necessary power of the shim magnet(s) to a point where the shim magnet(s) do not require water cooling.

In other implementations, the shim magnet(s) may be used to counteract the normal flux distribution around the main magnet, in contrast to the configurations discussed above that aid in the desired flux distribution for a high-fidelity field free line. With shim magnet(s) configured in this counteracting manner, the FFL can be reshaped into different forms, for example, into an approximation of a field-free point, or into an ellipsoidal field-free region. In such configurations, an FFL-type magnet may be configured to behave more like a field free point magnet, thus allowing for improved imaging in situations where signal from parts of a subject are preferably avoided (e.g., when seeking to minimize a large signal from the liver while trying to detect a small source near the liver). A control system associated with the magnetic particle imaging system can thus be configured to avoid excitation of a particular portion of the subject. In addition, such configurations can allow for increased spatial selectivity in hybrid imaging and magnetic actuation MPI systems.

In configurations where shim magnet(s) are configured to counteract the normal flux distribution around the main magnet, an ellipsoidal field free region can be created, thus allowing for beneficial slab imaging.

In some embodiments, such configurations of shim magnets that counteract the main magnet flux distribution, may require high power amplifiers, independent drive mechanisms and systems for cooling the shim magnets.

The present disclosure contemplates systems and methods for actively shimming the magnet (e.g., magnets 520, 530, 540, 550) during an imaging sequence.

Because of the non-linearity of the saturation of a flux return, the fidelity of FFL 140 can vary as magnet gradient strength varies. For example, FFL 140 can have a high level of fidelity at a particular gradient strength, but if an imaging sequence requires a change in the gradient strength, resulting changes to the magnetic flux distribution can negatively impact the fidelity of FFL 140. The present disclosure contemplates utilization of active shims, as discussed herein, to counteract the degradation in fidelity with the addition of shim magnet fields.

Similarly, while FFL 140 may have a high level of fidelity when located at the center of the imaging volume, as the FFL is shifted away from the center during imaging, the FFL can experience a degradation in fidelity. The present disclosure contemplates utilization of the active shims, as discussed herein, to counteract this degradation in fidelity.

In certain implementations of the shimming methods and shim magnets discussed herein, main field gradient fidelity can be designed with respect to a particular design field, and then deviations in strength and position from this design field can be compensated for by the use of shim magnet(s). The current in the shim magnets (and other magnets) can be set using a priori models, measured experimentally and set using a lookup table, and/or may be measured and adjusted in real-time using, for example, Hall-effect probes and feedback, or any combination thereof.

In certain embodiments, shim magnets contemplated by the present disclosure may also be configured to provide further localization of heating and energy deposition in three dimensions, for example, when the magnetic particle imaging system is configured for spatially-selective magnetic fluid hyperthermia/excitation applications. For example, reshaping a field-free line to a point-like or ellipsoidal field-free region can contain heating or actuation in this smaller region rather than along the entire line of a field-free line.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims.

The invention claimed is:

1. A Magnetic Particle Imaging (MPI) system comprising:
a magnet for the MPI system, the magnet configured to generate a magnetic field comprising:
a field free line within the magnetic field having an axis and a center; and
a first shim magnet centered approximately above the field free line, the first shim magnet configured to modify the magnetic field.

2. The magnetic particle imaging system of claim 1 further comprising a second shim magnet centered approximately below the field free line, the second shim magnet configured to modify the magnetic field.

3. The magnetic particle imaging system of claim 1 wherein the first shim magnet is a passive shim.

4. The magnetic particle imaging system of claim 1 wherein the first shim magnet is an active shim.

5. The magnetic particle imaging system of claim 1 further comprising an angled shim magnet pointed generally toward the field-free line.

6. The magnetic particle imaging system of claim 1 wherein the first shim magnet is elongate.

7. The magnetic particle imaging system of claim 1 wherein the first shim magnet is configured to decrease a gradient along the axis of the field-free line.

8. The magnetic particle imaging system of claim 1 wherein the first shim magnet is configured to improve the fidelity of the field-free line.

9. The magnetic particle imaging system of claim 7 wherein the magnet does not include a flux return.

10. The magnetic particle imaging system of claim 7 further comprising a flux return integrated with the magnet and wherein the first shim magnet does not require water cooling.

11. The magnetic particle imaging system of claim 1 wherein at least the first shim magnet is configured to reshape the field free line to approximate an ellipsoidal field-free region.

12. The magnetic particle imaging system of claim 11 further comprising a control system configured for imaging while avoiding excitation of a particular portion of a subject.

13. The magnetic particle imaging system of claim 11 further comprising a control system configured for increased spatial selectivity in hybrid imaging and magnetic actuation MPI.

14. The magnetic particle imaging system of claim 1 wherein at least the first shim magnet is configured to enable slab imaging.

15. The magnetic particle imaging system of claim 1 wherein at least the first shim magnet is configured to be actively controlled to counteract field free line fidelity degradation resulting from gradient strength changes.

16. The magnetic particle imaging system of claim 1 wherein at least the first shim magnet is configured to be actively controlled to counteract field free line fidelity degradation resulting from shifting of the field free line during imaging.

17. The magnetic particle imaging system of claim 1 further comprising the shim magnet configured to provide localized heating and energy deposition in three dimensions when the magnetic particle imaging system is configured for spatially-selective magnetic fluid hyperthermia applications.

\* \* \* \* \*